(12) United States Patent
Freund et al.

(10) Patent No.: US 8,822,938 B2
(45) Date of Patent: Sep. 2, 2014

(54) DETECTOR HAVING AN ARRAY OF PHOTODIODES

(75) Inventors: Andreas Freund, Heroldsbach (DE); Thomas Hilderscheid, Altdorf (DE)

(73) Assignee: Siemens Aktiengesellschaft, Munich (DE)

( * ) Notice: Subject to any disclaimer, the term of this patent is extended or adjusted under 35 U.S.C. 154(b) by 20 days.

(21) Appl. No.: 11/546,994

(22) Filed: Oct. 13, 2006

(65) Prior Publication Data

US 2007/0096033 A1    May 3, 2007

(30) Foreign Application Priority Data

Oct. 14, 2005    (DE) .......................... 10 2005 049 228

(51) Int. Cl.
*H01L 27/146* (2006.01)
*G01T 1/24* (2006.01)

(52) U.S. Cl.
CPC ........ *H01L 27/146* (2013.01); *H01L 27/14603* (2013.01)
USPC ............ 250/370.09; 250/370.11; 250/370.08; 250/208.1

(58) Field of Classification Search
CPC .................. H01L 27/14601; H01L 27/14603; H01L 27/14609; H01L 27/14659; H01L 27/14663; G01T 1/24
USPC .................. 250/370.09, 370.11, 559.05, 366, 250/208.1, 370.08, 367; 378/98.8, 19, 98.7; 348/302, 307, 308, 310, 222.1; 257/E27.131, E27.14, E5.086
See application file for complete search history.

(56) References Cited

U.S. PATENT DOCUMENTS

| | | | |
|---|---|---|---|
| 5,059,800 A | 10/1991 | Cueman et al. | |
| 5,196,692 A * | 3/1993 | Arinaga et al. | 250/208.1 |
| 5,329,124 A * | 7/1994 | Yamamoto et al. | 250/367 |
| 5,714,753 A * | 2/1998 | Park | 250/208.1 |
| 5,789,737 A * | 8/1998 | Street | 250/208.1 |
| 6,091,795 A | 7/2000 | Schafer et al. | |
| 6,144,718 A | 11/2000 | Hoffman et al. | |
| 6,452,153 B1 * | 9/2002 | Lauxtermann et al. | 250/208.1 |
| 6,734,906 B1 | 5/2004 | Hashimoto | |
| 6,759,641 B1 * | 7/2004 | Loose | 250/208.1 |

(Continued)

FOREIGN PATENT DOCUMENTS

| | | |
|---|---|---|
| DE | 19839787 A1 | 5/1999 |
| DE | 101 45 997 A1 | 4/2003 |

(Continued)

OTHER PUBLICATIONS

Laplante, P.A., Definition of Resolution, Frontmatter Electrical Engineering Dictionary, Boca Raton: CRC Press LLC 2000.*

(Continued)

*Primary Examiner* — David Porta
*Assistant Examiner* — Yara B Green
(74) *Attorney, Agent, or Firm* — Harness, Dickey & Pierce, P.L.C.

(57) ABSTRACT

A detector is disclosed, in particular for X-radiation. The detector includes an array of photodiodes, each respectively corresponding to a pixel with regard to size of their photosensitive receiving surface. Each photodiode is subdivided in the same way into at least two sub-photodiodes. Further, each photodiode includes at least one electric switch such that only one or all the sub-photodiodes of the photodiode are connectable to an evaluation circuit.

21 Claims, 3 Drawing Sheets

(56) References Cited

U.S. PATENT DOCUMENTS

| | | | |
|---|---|---|---|
| 6,838,674 B2* | 1/2005 | Otto | 250/370.11 |
| 6,839,407 B2 | 1/2005 | Nascetti et al. | |
| 7,260,174 B2* | 8/2007 | Hoffman et al. | 378/19 |
| 2003/0141564 A1* | 7/2003 | Kondo et al. | 257/442 |
| 2003/0164442 A1* | 9/2003 | Beusch | 250/208.1 |
| 2005/0104000 A1* | 5/2005 | Kindem et al. | 250/361 R |
| 2005/0285043 A1* | 12/2005 | Nascetti et al. | 250/370.09 |
| 2006/0045236 A1* | 3/2006 | Hoffman | 378/19 |
| 2006/0151818 A1* | 7/2006 | Toumiya | 257/294 |

FOREIGN PATENT DOCUMENTS

| | | |
|---|---|---|
| EP | 0 429 977 A2 | 6/1991 |
| EP | 1 312 938 A2 | 5/2003 |
| EP | 1 517 375 A2 | 3/2005 |
| JP | 10-224560 | 8/1998 |
| JP | 2004-093489 | 3/2004 |
| JP | 2005-034313 | 2/2005 |
| JP | 2005-526985 | 9/2005 |
| WO | WO 9919713 A1 | 4/1999 |
| WO | WO 03/100459 A1 | 12/2003 |

OTHER PUBLICATIONS

Japanese Office Action dated Nov. 1, 2011 for Application No. 2006-279747.

Chinese Office Action dated Jun. 3, 2010 for corresponding Chinese Patent Application No. 2006101309569 and English language translation thereof.

Japanese Office Action dated Jun. 24, 2012, issued in Japanese Patent Application No. 2006-279747 and English translation thereof.

* cited by examiner

DETECTOR HAVING AN ARRAY OF PHOTODIODES

PRIORITY STATEMENT

The present application hereby claims priority under 35 U.S.C. §119 on German patent application number DE 10 2005 049 228.2 filed Oct. 14, 2005, the entire contents of which is hereby incorporated herein by reference.

FIELD

The invention generally relates to a detector, for example for X-radiation. For example, it may relate to a detector including an array of photodiodes, which respectively correspond to a pixel with regard to the size of their photosensitive receiving surface.

BACKGROUND

In imaging with an X-ray unit, for example with an X-ray computed tomography unit, which has an X-ray recording system with an X-ray source and an X-ray detector, the aim is to design the detection surface of the X-ray detector which is available for image acquisition to be as large as possible in order, for example, to be able to scan whole organs, such as the heart of a patient, in one course of the X-ray system. Such an X-ray detector, also denoted as a flat detector, is constructed as a rule from a multiplicity of detector modules that are aligned with respect to one another in two dimensions. Each detector module has an array of scintillator elements and an array of photodiodes that are aligned with respect to one another. A scintillator element and a photodiode in this case form a detector element of the detector module. A detector element represents a pixel of the detector. The scintillator elements convert X-radiation impinging on them into visible light that is converted into electric signals by the downstream photodiodes of the array of photodiodes.

In specific instances of medical diagnosis, it is desirable to be able to use the X-ray machine to produce images of an examination object that have a higher spatial resolution than the spatial resolution of the X-ray detector used, which spatial resolution is prescribed by the raster of the detector elements or the raster of the pixels. For this purpose, it is known from DE 101 45 997 A1 to use a high resolution diaphragm that has closely adjacent diaphragm slots and is formed from a material, usually from a heavy metal, that absorbs X-rays. The high resolution diaphragm shades a portion of each pixel of the array of scintillator elements such that in each case X-radiation is applied only to a portion of a scintillator element, the result being to achieve a higher spatial resolution. In order to achieve a higher spatial resolution, however, only a portion of the X-radiation which has passed through the patient is used for imaging.

In order, in addition to X-ray pictures with a spatial resolution corresponding to the raster of the pixels, also to be able to obtain X-ray pictures of higher spatial resolution, the high resolution diaphragm can, as a rule, be moved by motor between an operating position and an axially offset non-operational position. Consequently, on the X-ray recording system there is additionally a moving component, specifically the high resolution diaphragm, which has to be adjusted for operation, and for which additional resolution space must be made available on the X-ray recording system in order, in the case of nonuse, to be able to take up the high resolution diaphragm such that it is not prevented from acquiring other images using the X-ray recording system. Moreover, moving the high resolution diaphragm into an operating position and into a non-operational position requires a complicated and very expensive mechanism.

SUMMARY

In at least one embodiment of the invention, a detector is specified in such a way that the detector can be used for X-ray pictures of higher spatial resolution without having to use a high resolution diaphragm.

In at least one embodiment of the invention, a detector includes an array of photodiodes, which respectively correspond to a pixel with regard to the size of their photosensitive receiving surface, each photodiode being subdivided in the same way into at least two sub-photodiodes, and each photodiode having at least one electric switch such that only one or all the sub-photodiodes of the photodiode are connectable to an evaluation circuit. Thus, in at least one embodiment, it is proposed that the photosensitive receiving surface of each photodiode of the array, which corresponds to a pixel, be divided again into at least two sub-photodiodes, and that the photodiode be provided with a switch such that only one sub-photodiode is active for recording X-ray projections of high spatial resolution, and that all the sub-photodiodes are active in the case of recording X-ray projections of normal spatial resolution, which would correspond to the conventional operation of the photodiode. It is possible in this way to obtain X-ray projections of increased spatial resolution without the need to use a special high resolution diaphragm in order respectively to shade a portion of the detector surface so as to obtain X-ray projection of increased spatial resolution.

According to a variation of an embodiment of the invention, the switch is a switch using CMOS technology and which can easily be integrated in a photodiode. The switch may be operated, for example, under the control of the evaluation circuit such that, depending on the operating mode of the detector, either all the sub-photodiodes of a photodiode contribute to the signal generation of the photodiode, or that respectively only a specific sub-photodiode of a photodiode is active in order to obtain the X-ray projection of increased spatial resolution.

According to an example embodiment of the invention, each photodiode is subdivided into a first and into a second sub-photodiode, the first sub-photodiode being of substantially square or rectangular design with regard to its photosensitive receiving surface. According to one variant of an embodiment of the invention, the second sub-photodiode is of substantially L-shaped design with regard to its photosensitive receiving surface. The first sub-photodiode and the second sub-photodiode preferably supplement one another to form a substantially square or rectangular photodiode of the array of photodiodes. It is possible in this way to enable X-ray projections to be recorded with an increased spatial resolution by subdividing a conventional photodiode into only two sub-photodiodes. In this case, the first sub-photodiode used for the increased spatial resolution has a substantially square or rectangular shape, just as a conventional photodiode also intrinsically has.

According to one embodiment of the invention, the array of photodiodes is assigned an array of scintillator elements aligned relative to the array of photodiodes such that a photodiode is respectively assigned a scintillator element. The scintillator elements are respectively subdivided into at least two sub-elements. The subdivision of the scintillator elements into sub-elements can be performed in this case in the same way as the subdivision of the photodiode into sub-photodiodes. In order to simplify the production of the array of scintillator elements, the scintillator elements are subdivided into four sub-elements, particularly with regard to the square or rectangular design of the first sub-photodiode and the L-shaped design of the second sub-photodiode. According to variations of embodiments of the invention, in this case precisely one sub-element of a scintillator element is assigned to the first sub-photodiode, and the remaining sub-elements of the scintillator element are assigned to the second photodiode.

Embodiments of the invention provide that the scintillator elements and the sub-elements are separated from one another by slots that are filled with an optically reflecting material, the slots between the scintillator elements being wider than the slots between the sub-elements. The result of this is that the array of scintillator elements is structured in a fashion adapted to the array of the photodiodes.

According to one embodiment of the invention, the detector has a number of detector modules with in each case an array of scintillator elements and an array of photodiodes of which at least one includes an array of photodiodes whose photodiodes are subdivided in the same way into at least two sub-photodiodes. Thus, the detector need not completely exhibit such detector modules, but can also partially comprise conventionally designed detector modules, which are to be understood as detector modules whose photodiodes and scintillator elements are not further subdivided.

The detector is provided, for example for an X-ray machine, for example for an X-ray computed tomography unit.

BRIEF DESCRIPTION OF THE DRAWINGS

Example embodiments of the invention are discussed below and are illustrated in the attached schematics, in which.

DETAILED DESCRIPTION OF THE EXAMPLE EMBODIMENTS

Figure 1:
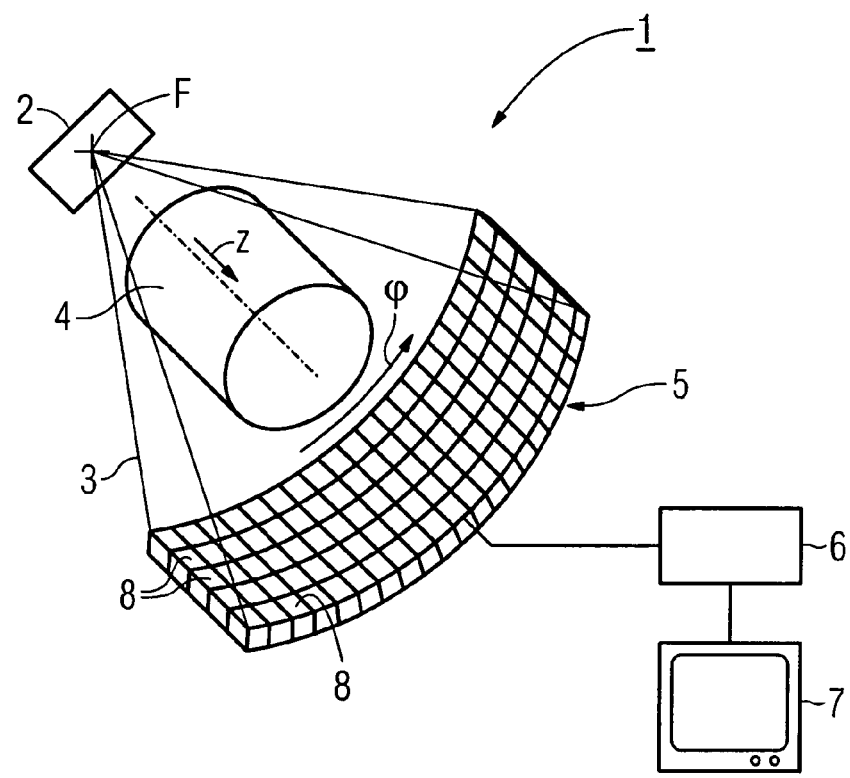
FIG. 1 shows a schematic of a computed tomography unit, partially as a block diagram.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

FIG. 1 shows a schematic of a computed tomography unit 1, partially as a block diagram. The computed tomography unit 1 includes an X-ray source 2 from the focus F of which there emanates an X-ray beam 3 that is shaped, for example as a fan or pyramid, with the aid of diaphragms that are not illustrated in FIG. 1 but are known per se. The X-ray beam 3 penetrates an object 4 to be examined and impinges on an X-ray detector 5.

The X-ray source 2 and the X-ray detector 5 are arranged, in a way not illustrated in FIG. 1, situated opposite one another on a rotary frame of the computed tomography unit 1, which rotary frame can be rotated in the $\Phi$-direction about the system axis Z of the computed tomography unit 1. During operation of the computed tomography unit 1, the X-ray source 2, arranged on the rotary frame, and the X-ray detector 5 rotate about the object 4, X-ray pictures of the object 4 being obtained from different projection directions. In this case, for each X-ray projection, X-radiation that has passed through the object 4 and has been attenuated thereby strikes the X-ray detector 5, the X-ray detector 5 generating signals that correspond to the intensity of the impinged X-radiation. Subsequently, in a way known per se an image computer 6 uses the signals determined with the aid of the X-ray detector 5 to calculate one or more two- or three-dimensional images of the object 4 that can be displayed on a monitor 7.

In the case of the present example embodiment, the X-ray detector 5 has a multiplicity of detector modules 8 that are arranged next to one another in the $\Phi$-direction and in the z-direction on a detector arc, which is not illustrated in more detail and is fastened on the rotary frame, and form the planar X-ray detector 5 in the case of the present example embodiment.

Figure 2:
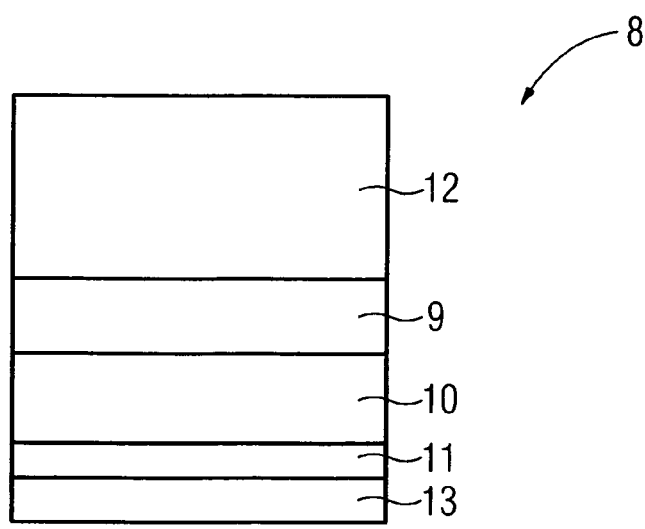
FIG. 2 shows a detector module of the computed tomography unit from FIG. 1.

A detector module 8 of the X-ray detector 5 is shown in FIG. 2 by way of example. The detector module 8 has a vertical structure, an array of scintillator elements 9 being arranged above an array of photodiodes 10 based on semiconductors. A collimator 12 is present above the array of scintillator elements 9 such that only X-radiation from a specific spatial direction can reach the array of scintillator elements 9.

In the case of the present example embodiment, the array of photodiodes 10 is arranged on a printed circuit board 11 on whose other side are located electrical components that are not illustrated in more detail and which belong to an evaluation circuit 13, and which preprocess the electric signals generated by the photodiodes of the array of photodiodes 10. The preprocessed signals are subsequently transmitted, in a way not illustrated explicitly, for example, with the aid of sliprings, from the rotary frame to the computer 6, which reconstructs two-dimensional tomographs or three-dimensional images of the object 4, for example.

Figure 3:
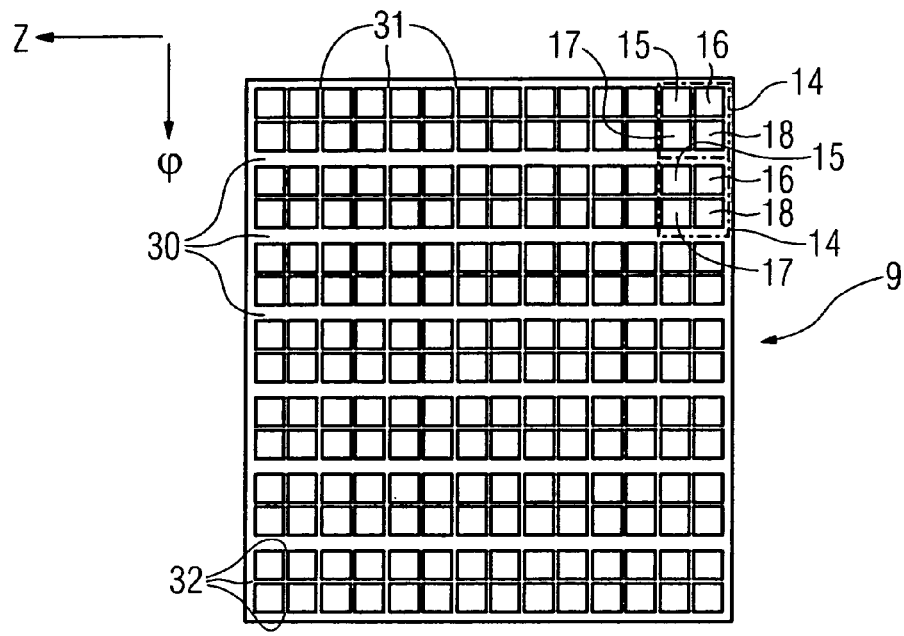
FIG. 3 shows a plan view of the array of scintillator elements of the detector module from FIG. 2.

The array of scintillator elements 9 has been structured in the way shown in FIG. 3 in order to be able to use the computed tomography unit 1 to generate images of the object 4 with a higher spatial resolution than is prescribed by the raster of the pixels. FIG. 3 shows here a plan view of the array of scintillator elements 9 from FIG. 2. As is to be seen from FIG. 3, the array of scintillator elements 9 includes a multiplicity of scintillator elements 14 that are arranged in rows running in the $\Phi$-direction and in columns running in the z-direction and of which each represents a pixel, and which are of substantially square design with regard to their radiation-sensitive receiving surface in the case of the present example embodiment.

In the case of the present example embodiment, the scintillator elements 14 are once again respectively subdivided into four sub-elements 15, 16, 17, 18, likewise of square design. The array of scintillator elements 9 results in this case from structuring a wafer-shaped scintillator ceramic, slots 30, 31, 32 having been introduced into the scintillator ceramic by way of sawing in order to form the scintillator elements 14 and the sub-elements 15, 16, 17, 18. The slots are subsequently filled with an optically reflecting material in order largely to avoid optical crosstalk between the scintillator elements 14, on the one hand, and the sub-elements 15, 16, 17, 18, on the other hand.

As may be seen from FIG. 3, the array of scintillator elements 9 is structured in the case of the present example embodiment in such a way that the slots 30 filled with the reflecting material, between the scintillator elements 14, which are also denoted as septa, have a greater width in the Φ-direction than the septa 31 present between the scintillator elements 14 in the z-direction. Whereas the width of the slots 30 between the scintillator elements 14 in the Φ-direction is approximately 300 μm, the slots 31 between the scintillator elements 14 in the z-direction have a width of approximately 80 μm. Within a scintillator element 14, the width of the slots 32 between the sub-elements 15, 16, 17, 18 is once again substantially less, being between 30 and 40 μm.

Figure 4:
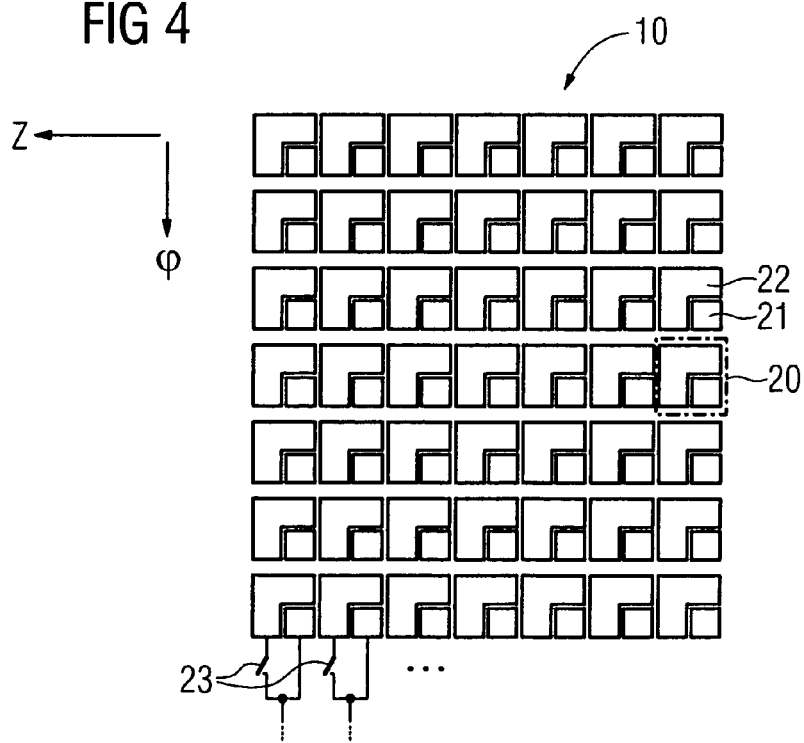
FIG. 4 shows a plan view of the array of photodiodes of the detector module from FIG. 2, and FIGS. 5 and 6 show various embodiments of photodiodes.

FIG. 4 shows a plan view of the array of photodiodes 10 aligned relative to the array of scintillator elements 9. The array of photodiodes 10 includes a multiplicity of photodiodes 20 that are arranged in rows running in the Φ-direction and in columns running in the z-direction and which are of substantially square design with regard to their photosensitive receiving surface. The shape and size of the photosensitive receiving surface of a photodiode 20 corresponds in this case substantially to the shape and size of the radiation-sensitive receiving surface of a scintillator element 14. Here, in each case a scintillator element 14 and the photodiode 20 assigned to it form a detector element that embodies a pixel of the X-ray detector 5.

As already mentioned, in order to be able to use the computed tomography unit 1 to obtain images of increased spatial resolution, in the case of the present exemplary embodiment the array of photodiodes 10 is designed in such a way that each photodiode 20 is subdivided in the same way into at least two sub-photodiodes, something which is achieved by means of appropriate doping of the semiconductor material used to produce the array of photodiodes 10. Whereas the first sub-photodiode 21 is of substantially square design with regard to its photosensitive receiving surface, the second sub-photodiode 22 is substantially in the shape of a L with regard to its photosensitive receiving surface. As may be gathered from FIG. 4, the two sub-photodiodes 21 and 22 complement one another to form a photodiode 20 that is of substantially square design.

As may be gathered by way of example from FIG. 4 with the aid of two photodiodes 20, in the case of the present example embodiment all the photodiodes 20 of the array of photodiodes 10 have a switch 23 that is, for example, implemented using CMOS technology. The switches 23 permit the array of photodiodes 10 to be operated in terms of two operating modes.

In the first operating mode, in which the switch is closed, both the first sub-photodiode 21 and the second sub-photodiode 22 contribute to the signal generation. In this case, the X-ray detector 5 or, specifically, the array of photodiodes 10 is operated virtually conventionally, as if there were no subdivision of the photodiodes 20. The spatial resolution corresponds in this case to the spatial resolution prescribed by the raster of the scintillator elements 14 and the congruent raster of the photodiodes 20.

If, by contrast, the switches 23 of the photodiodes 20 are opened, it is respectively only the first sub-pixels that are respectively formed by the first sub-photodiode 21 and the sub-element 18 that contribute to the signal generation. The L-shaped second sub-photodiode 22, to which the remaining sub-elements 15, 16, 17 of the assigned scintillator element 14 are assigned, makes no contribution to the imaging. Consequently, images of the object 4 that have an increased spatial resolution can be obtained in this second operating mode of the array of photodiodes 10. The closing and opening of the switches 23 is preferably controlled via the evaluation circuit 13, to which end corresponding control lines (not illustrated explicitly) are present.

Figure 5:
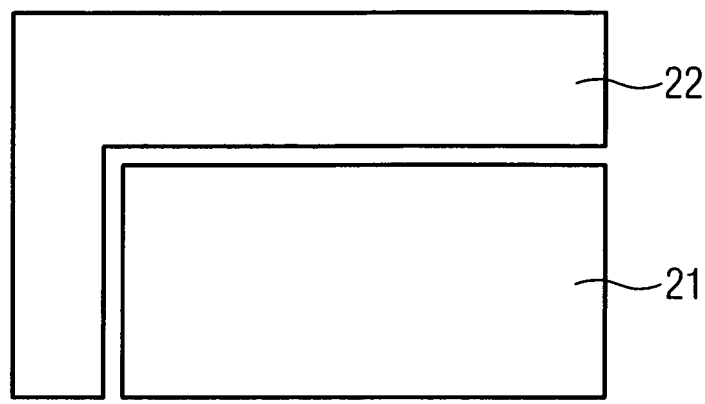

In the case of the present example embodiment, the scintillator elements 14 of the array of scintillator elements 9 are structured in such a way, the photodiodes 20 of the array of photodiodes 10 are subdivided, and the two arrays are aligned relative to one another such that in each case the lower right-hand sub-element 18 of the first sub-photodiode 21, and the remaining sub-elements 15, 16, 17 of a scintillator element 14 are assigned to the second sub-photodiode 22. However, the subdivision of a photodiode 20 as shown in FIG. 4, and the arrangement of a scintillator element 14 as shown in FIG. 3 are to be understood purely by way of example. Thus, a photodiode 20 can also be subdivided into sub-photodiodes in a different way, as is illustrated by way of example in FIGS. 5 and 6. For example, the first sub-photodiode can have a rectangular shape, and the second sub-photodiode can be in the shape of a L, as may be gathered from FIG. 5.

Figure 6:
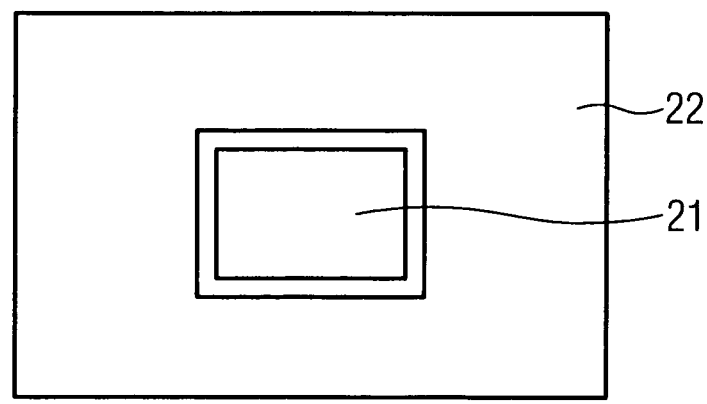

However, as is to be gathered from FIG. 6, it is also possible for the first sub-photodiode to be of substantially square or rectangular design, and for the second sub-photodiode to be in the shape of a frame, the second sub-photodiode surrounding the first sub-photodiode. Apart from these additional example embodiments of subdivided photodiodes, it is also possible to conceive further ones without departing from the idea of the invention, it being necessary, if appropriate, to adapt the structuring of the scintillator elements correspondingly depending on the subdivision of the photodiode into sub-photodiodes.

Embodiments of the invention were described above on the example of an X-ray computed tomography unit. However, the embodiments of the invention are not limited to an X-ray computed tomography unit. However, it is also possible for other X-ray machines to have a detector with photodiodes designed in such a way.

Furthermore, the embodiments of invention can be applied outside the field of medical technology.

If it is advantageous, a photodiode can also have a number of switches in order, for example, to be able to operate both sub-photodiodes independently of one another.

Furthermore, a photodiode can also be subdivided into more than two sub-photodiodes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:
1. An x-ray detector comprising:
a pixelated array of x-ray scintillator elements; and a pixelated array of photodiodes, each x-ray scintillator element being assigned to a single photodiode, each photodiode corresponding to a single pixel, wherein each photodiode includes a photosensitive receiving surface, the photodiode being subdivided into at least two different sized sub-photodiodes by appropriately doping a semiconductor material forming the pixilated array of photodiodes with respect to the photosensitive receiving surface, each sub-photodiode being smaller than the photodiode and the photosensitive receiving surface of the photodiode corresponding to a receiving surface of the corresponding x-ray scintillator element, each photodiode including at least one electric switch configured to couple the sub-photodiodes of the photodiode such that at least one of the sub-photodiodes is connectable to an evaluation circuit, and the x-ray detector being configured to provide a dual spatial resolution for x-ray projections, wherein by connecting only one sub-photodiode of each photodiode to the evaluation circuit, the x-ray detector is arranged for acquiring x-ray projections in a high spatial resolution mode, the only one sub-photodiode being a smallest sub-photodiode in each photodiode with respect to the photosensitive receiving surface of the photodiode, the only one sub-photodiode contributing to signal generation and imaging in the high spatial resolution mode, and by connecting all the sub-photodiodes to the evaluation circuit, the x-ray detector is arranged for acquiring x-ray projections in a low spatial resolution mode, all the sub-photodiodes contribute to signal generation and imaging in the low spatial resolution mode.

2. The x-ray detector as claimed in claim 1, wherein the switch is a switch using CMOS technology.

3. The x-ray detector as claimed in claim 2, wherein each photodiode is subdivided into a first and into a second sub-photodiode, the first sub-photodiode being of at least one of substantially square and substantially rectangular design with regard to its photosensitive receiving surface.

4. The x-ray detector as claimed in claim 3, wherein the second sub-photodiode is of substantially L-shaped design with regard to its photosensitive receiving surface.

5. The x-ray detector as claimed in claim 2, wherein each photodiode is respectively assigned a single x-ray scintillator element, the x-ray scintillator elements respectively being subdivided into at least two sub-elements.

6. The x-ray detector as claimed in claim 5, wherein at least one of the x-ray scintillator elements is subdivided into four sub-elements.

7. The x-ray detector as claimed in claim 1, wherein each photodiode is subdivided into a first and into a second sub-photodiode, the first sub-photodiode being of at least one of substantially square and substantially rectangular design with regard to its photosensitive receiving surface.

8. The x-ray detector as claimed in claim 7, wherein the second sub-photodiode is of substantially L-shaped design with regard to its photosensitive receiving surface.

9. The x-ray detector as claimed in claim 1, wherein each photodiode is respectively assigned a single x-ray scintillator element, the x-ray scintillator elements respectively being subdivided into at least two sub-elements.

10. The x-ray detector as claimed in claim 9, wherein at least one of the x-ray scintillator elements is subdivided into four sub-elements.

11. The x-ray detector as claimed in claim 10, wherein precisely one sub-element of the x-ray scintillator element is assigned to the first sub-photodiode.

12. The x-ray detector as claimed in claim 11, wherein the remaining sub-elements of the x-ray scintillator element are assigned to the second sub-photodiode.

13. The x-ray detector as claimed in claim 9, wherein precisely one sub-element of the x-ray scintillator element is assigned to the first sub-photodiode.

14. The x-ray detector as claimed in claim 13, wherein the remaining sub-elements of the x-ray scintillator element are assigned to the second sub-photodiode.

15. The x-ray detector as claimed in claim 14, wherein the x-ray scintillator elements and the sub-elements are separated from one another by slots that are filled with an optically reflecting material.

16. The x-ray detector as claimed in claim 15, wherein the slots between the x-ray scintillator elements are relatively wider than the slots between the sub-elements.

17. The x-ray detector as claimed in claim 9, wherein the x-ray scintillator elements and the sub-elements are separated from one another by slots that are filled with an optically reflecting material.

18. The x-ray detector as claimed in claim 17, wherein the slots between the x-ray scintillator elements are relatively wider than the slots between the sub-elements.

19. The x-ray detector as claimed in claim 1, further comprising a number of detector modules that comprise an array of x-ray scintillator elements and an array of photodiodes, at least one detector module including the array of photodiodes whose photodiodes are subdivided in the same way into at least two sub-photodiodes.

20. An X-ray machine, comprising the x-ray detector as claimed in claim 1.

21. An X-ray computed tomography unit, comprising the x-ray detector as claimed in claim 1.

* * * * *